(12) United States Patent
Friesz et al.

(10) Patent No.: US 9,611,242 B2
(45) Date of Patent: *Apr. 4, 2017

(54) PROCESS FOR PREPARATION OF DRONEDARONE BY N-BUTYLATION

(71) Applicant: SANOFI, Paris (FR)

(72) Inventors: Antal Friesz, Budapest (HU); Zsolt Párkányi, Budapest (HU); Zsolt Dombrády, Budapest (HU)

(73) Assignee: SANOFI, Paris (FR)

( * ) Notice: Subject to any disclaimer, the term of this patent is extended or adjusted under 35 U.S.C. 154(b) by 0 days.

This patent is subject to a terminal disclaimer.

(21) Appl. No.: 14/863,206

(22) Filed: Sep. 23, 2015

(65) Prior Publication Data

US 2016/0009679 A1     Jan. 14, 2016

Related U.S. Application Data

(62) Division of application No. 14/007,814, filed as application No. PCT/HU2012/000020 on Mar. 27, 2012, now Pat. No. 9,174,959.

(30) Foreign Application Priority Data

Mar. 29, 2011   (HU) .................................. 1100165

(51) Int. Cl.
  *C07D 487/04*   (2006.01)
  *C07D 307/81*   (2006.01)
  *C07D 307/80*   (2006.01)

(52) U.S. Cl.
  CPC ......... *C07D 307/81* (2013.01); *C07D 307/80* (2013.01)

(58) Field of Classification Search
  CPC .................................................. C07D 487/04
  See application file for complete search history.

(56) References Cited

U.S. PATENT DOCUMENTS

| | | |
|---|---|---|
| 3,577,441 A | 5/1971 | Kaminsky et al. |
| 3,657,350 A | 4/1972 | Mooradian et al. |
| 3,937,737 A | 2/1976 | Eiglmeier |
| 4,243,405 A | 1/1981 | Balasubramanyan et al. |
| 4,666,931 A | 5/1987 | Ohishi et al. |
| 5,066,803 A | 11/1991 | D'Ambra et al. |
| 5,223,510 A | 6/1993 | Gubin et al. |
| 6,555,697 B1 | 4/2003 | Schlama |
| 6,828,448 B2 | 12/2004 | Fino et al. |
| 6,846,936 B2 | 1/2005 | Biard |
| 6,855,842 B1 | 2/2005 | Schlama et al. |
| 6,949,583 B2 | 9/2005 | Assens et al. |
| 6,984,741 B2 | 1/2006 | Magerlein |
| 7,148,240 B2 | 12/2006 | Assens et al. |
| 7,312,345 B2 | 12/2007 | Gutman et al. |
| 7,517,876 B2 | 4/2009 | Klein et al. |
| 8,143,269 B2 | 3/2012 | Whitten et al. |
| 8,501,971 B2 | 8/2013 | Friesz et al. |
| 8,658,808 B2 | 2/2014 | Kretzschmar et al. |
| 8,658,809 B2 | 2/2014 | Friesz et al. |
| 8,674,121 B2 | 3/2014 | Kretzschmar et al. |
| 8,686,180 B2 | 4/2014 | Bon et al. |
| 8,748,636 B2 | 6/2014 | Bailly et al. |
| 8,796,489 B2 | 8/2014 | Bailly et al. |
| 8,816,103 B2 | 8/2014 | Friesz et al. |
| 8,871,956 B2 | 10/2014 | Bailly et al. |
| 8,884,033 B2 | 11/2014 | Bon et al. |
| 8,889,734 B2 | 11/2014 | Friesz et al. |
| 8,927,743 B2 | 1/2015 | Vishnu Newadkar et al. |
| 8,962,869 B2 | 2/2015 | Grimaud et al. |
| 9,024,046 B2 | 5/2015 | Friesz et al. |
| 9,174,958 B2 | 11/2015 | Friesz |
| 9,174,959 B2 | 11/2015 | Friesz et al. |
| 9,238,636 B2 | 1/2016 | Huszar et al. |
| 2008/0033209 A1 | 2/2008 | Szarvas et al. |
| 2010/0273764 A1 | 10/2010 | Andrews et al. |
| 2013/0023678 A1 | 1/2013 | Priem et al. |
| 2014/0018553 A1 | 1/2014 | Grimaud et al. |
| 2014/0081035 A1 | 3/2014 | Friesz et al. |
| 2015/0005515 A1 | 1/2015 | Friesz et al. |

(Continued)

FOREIGN PATENT DOCUMENTS

| | | |
|---|---|---|
| CN | 101838252 A | 9/2010 |
| CN | 101993427 A | 3/2011 |

(Continued)

OTHER PUBLICATIONS

The Royal Society of Chemistry. "Based on Handbook of Pharmaceutical Salts." © 2005.*
Abramenko et al. (1975). "Polymethine Dyes—Furo[2,3-g] Benzothiazole Derivatives," Chemistry of Heterocyclic Compounds 11:1361-1364.
Adams et al. (1951). Quinone imides. IV. P-Quinone monosulfonimides. Journal of the American Chemical Society 73:1145-1149.

(Continued)

*Primary Examiner* — Noble Jarrell
*Assistant Examiner* — John S Kenyon
(74) *Attorney, Agent, or Firm* — Morrison & Foerster LLP

(57) ABSTRACT

The invention relates to a compound of formula (II)

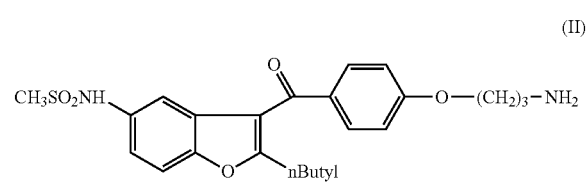

and salts thereof. Also described herein are processes for the preparation of a compound of formula (II) and pharmaceutically acceptable salts thereof.

2 Claims, No Drawings

(56) References Cited

U.S. PATENT DOCUMENTS

| | | |
|---|---|---|
| 2015/0018568 A1 | 1/2015 | Friesz |
| 2015/0031901 A1 | 1/2015 | Bon et al. |
| 2015/0031902 A1 | 1/2015 | Huszar et al. |
| 2015/0274688 A1 | 10/2015 | Huszar et al. |
| 2016/0009678 A1 | 1/2016 | Huszar et al. |

FOREIGN PATENT DOCUMENTS

| | | |
|---|---|---|
| EP | 0 471 609 A1 | 2/1992 |
| EP | 0 735 083 A1 | 10/1996 |
| FR | 2 833 259 A1 | 6/2003 |
| GB | 1064959 A | 4/1967 |
| WO | WO-96/05190 A1 | 2/1996 |
| WO | WO-02/48078 A1 | 6/2002 |
| WO | WO-02/48132 A1 | 6/2002 |
| WO | WO-03/040120 A1 | 5/2003 |
| WO | WO-03/048144 A2 | 6/2003 |
| WO | WO-03/048144 A3 | 12/2003 |
| WO | WO-2005/012301 A1 | 2/2005 |
| WO | WO-2007/022501 A2 | 2/2007 |
| WO | WO-2007/022501 A3 | 2/2007 |
| WO | WO-2007/100295 A1 | 9/2007 |
| WO | WO-2007/116111 A1 | 10/2007 |
| WO | WO-2007/133637 A2 | 11/2007 |
| WO | WO-2007/133637 A3 | 11/2007 |
| WO | WO-2007/140989 A2 | 12/2007 |
| WO | WO-2007/140989 A3 | 12/2007 |
| WO | WO-2009/044143 A2 | 4/2009 |
| WO | WO-2009/044143 A3 | 4/2009 |
| WO | WO-2010/038029 A1 | 4/2010 |
| WO | WO-2010/040261 A1 | 4/2010 |
| WO | WO-2010/116140 A1 | 10/2010 |
| WO | WO-2010/136501 A1 | 12/2010 |
| WO | WO-2010/136502 A1 | 12/2010 |
| WO | WO-2011/070380 A1 | 6/2011 |
| WO | WO-2011/099010 A1 | 8/2011 |
| WO | WO-2011/104591 A1 | 9/2011 |
| WO | WO-2011/107705 A1 | 9/2011 |
| WO | WO-2011/158050 A1 | 12/2011 |
| WO | WO-2012/004658 A2 | 1/2012 |
| WO | WO-2012/004658 A3 | 1/2012 |
| WO | WO-2012/010788 A1 | 1/2012 |
| WO | WO-2012/010802 A1 | 1/2012 |
| WO | WO-2012/010913 A1 | 1/2012 |
| WO | WO-2012/032545 A1 | 3/2012 |
| WO | WO-2012/127173 A1 | 9/2012 |
| WO | WO-2012/131408 A1 | 10/2012 |
| WO | WO-2012/131409 A1 | 10/2012 |
| WO | WO-2012/131410 A1 | 10/2012 |
| WO | WO-2013/014478 A1 | 1/2013 |
| WO | WO-2013/014479 A1 | 1/2013 |
| WO | WO-2013/014480 A1 | 1/2013 |
| WO | WO-2013/121234 A1 | 8/2013 |
| WO | WO-2013/121235 A2 | 8/2013 |
| WO | WO-2013/121235 A3 | 8/2013 |
| WO | WO-2013/128294 A2 | 9/2013 |
| WO | WO-2013/128294 A3 | 9/2013 |
| WO | WO-2013/128294 A8 | 9/2013 |

OTHER PUBLICATIONS

Adams et al. (1956). "Quinone Imides. XXXIX. Adducts of Quinone Monoimides and Conversion of Active Methylene Adducts to Benzofurans," *J. Am. Chem. Soc.* 78(3):658-663.

Alcaraz et al. (2004). "Novel N-Aryl and N-Heteroaryl Sulfamide Synthesis via Palladium Cross Coupling," Organic Letters 6(16):2705-2708.

Ando et al. (1982). "Motion at the Active Site of Tosylchymotrypsin," *Journal of the American Chemical Society* 104(11):3172-3178.

Anjanappa et al. (2008). "2-(Trimethylsilyl)ethanesulfonyl amide as a new ammonia equivalent for palladium-catalyzed amination of aryl halides," Tetrahedron Letters 49:4585-4587.

Bartoli et al. (1991). "Unexpected Elimination to α,β-Alkynylketones in the Reaction of Dianions of 1-Arylenaminones with Trimethylchlorosilane," Tetrahedron Letters 32(48):7091-7092.

Batra et al. (2001). "Syntheses and Biological Evaluation of Alkanediamines as Antioxidant and Hypolipidemic Agents," Bioorganic & Medicinal Chemistry 9(12):3093-3099.

Bavin (1973). "2-Aminofluorene," *Org. Syn. Coll.* 5:30.

Berthold et al. (2002). "Transfer Hydrogenation in Ionic Liquids under Microwave Irradiation," *Syn.* 1607-1610.

Boovanahalli et al. (2004). "Application of Ionic Liquid Halide Nucleophilicity for the Cleavage of Ethers: A Green Protocol for the Regeneration of Phenols from Ethers," Journal of Organic Chemistry 69:3340-3344.

Bourgery et al. (1981). "Synthesis and Antiarrhythmic Activity of New Benzofuran Derivatives," Journal of Medicinal Chemistry 24(2):159-167.

Burton et al. (2003). "Palladium-Catalyzed Intermolecular Coupling of Aryl Chlorides and Sulfonamides under Microwave Irradiation," Organic Letters 5(23):4373-4376.

Castellino et al. (1984). "Synthesis of Benzofurans from Oxygenated Phenoxyamines," Journal of Organic Chemistry 49:4399-4404.

Chauhan et al. (2004). "Microwave assisted dealkylation of alkyl aryl ethers in ionic liquids," Journal of Chemical Research, pp. 693-694.

Cheng et al. (2007). "Facile Cleavage of Ethers in Ionic Liquid," Bulletin of the Chemical Society of Japan 80(10):2008-2010.

Database PubChem Compound [Online] (Oct. 25, 2006),"CID 10095002—Compound Summary:N-[3-[4-(3-aminopropoxy) benzoyl)-2-butyl-1-benzofuran-5-yl", XP002676507 , Database accession No. 15082344. Retrieved from the Internet: URL:http://pubchem.ncbi.nlm.nih.gov/summary/summary.cgi?sid=15082344 &viewopt=PubChem [retrieved on May 23, 2012].

Delahay et al. (2007). "Past and Recent Approaches of Preparing Fe-ZSM-5," *Current Topics in Catalysis* 6:19-33.

Douglass (1959). "Some New Reactions of Methanesulfenyl Chloride," *Journal of Organic Chemistry* 24:2004-2006.

Denmark et al. (2008). "Lewis base catalysis in organic synthesis," *Angew. Chem. Int. Ed.* 47(9):1560-1638.

Fennel (1958). "Quinoline Analogs of Podophyllotoxin. I. Preliminary Experiments. Syntheses of Some 4-Phenylquinoline Derivatives," J. Org. Chem. 23:432-434.

Fieser et al. (1967). "Reagents for Organic Synthesis," John Wiley & Sons, pp. 703-705.

Fontana (2008). "Syntheses of (R,S)-Naproxen and its 6-O-Desmethyiated metabolite labelled with 2H," *J. Labelled Compounds and Radiopharma.* 51:239-241.

Gilow et al. (Jun.-Jul. 1991). "Sulfenylation of Some Pyrroles and Indoles," *J. Het. Chem.* 28:1025-1034.

Groves (1972). "The Friedel—Crafts Acylation of Alkenes," Chem. Soc. Rev. 1:73-97.

Gutowski et al, (2005). "Prediction of the Formation and Stabilities of Energetic Salts and Ionic Liquids Based on ab lnitio Electronic Structure Calculations," The Journal of Physical Chemistry B 109:23196-23208.

Haddadin et al. (1976). "Reaction to Benzofurazan Oxide with Unsymmetrical 1, 3-Diketones: Steric Polar Effects," *Tetrahedron* 32:719-724.

Hauser et al. (1948) "Alkaline cleavage of unsymmetrical β-diketones. Ring opening of acylcyclohexanones to form ε-acylcaproic acids," Journal of the American Chemical Society. 70:4023-4026.

Headley et al. (2006). "Dynamic Solvation in Imidazolium-Based Ionic Liquids on Short Time Scales," Journal of Physical Chemistry 110:9549-9554.

Horton et al. (1967). "Reactions With Reactive Alkyl Halides," *J. Meth. In Enzymology* 11:556-565.

Ikawa et al. (2007). "Pd-Catalyzed Amidations of Aryl Chlorides Using Monodentate Biaryl Phosphine Ligands: A Kinetic, Computational, and Synthetic Investigation," Journal of the American Chemical Society 129:13001-13007.

(56) References Cited

OTHER PUBLICATIONS

Imori et al. (2006). "Efficient Demethylation of N,N-Dimethylanilines with Phenyl Chloroformate in Ionic Liquids," *Synlett.* 16:2629-2632.
International Search Report dated Jun. 12, 2012 issued in PCT/HU2012/000020.
Johnson Matthey Handbook of Pharmaceutical Catalysis, 2009, pp. 1-106.
Joshi et al. (1986). "Some New Fluorinated β-Ketoamines and Their Copper Complexes," Synth. React. lnorg. Met. -Org. Chem. 16(7):1009-1024.
Krongauz et al. (1986). Poly(anilophenylquinoxaline)s. Inst. Elementoorg. Soedin. 28(4):771 (Abstract).
Kurti et al. (2005). Strategic Applications of Named Reactions in Organic Synthesis. El Sevior, pp. 448-449.
Kwiatkowski et al. (1978). "Metal Benzoylpivaloylmethanates, Part I. Free Ligands and Copper(II) Chelates," Transition Met. Chem. 3:305-308.
Laszlo et al. (1987). "Catalysis of Friedel-Crafts Alkylation by a Montmorillonite Doped with Transition-Metal Cations," Helvetica Chimica Acta 70:577-586.
Liu et al. (2004). "Cleavage of Methyl Ethers of Flavones by Chloroaluminate Ionic Liquid," Synthetic Communications 34:3209-3218.
Majdik (1985). "Studiul reactiei de ciclizare a orto-hidroxibenzilfenilcetonelor in benzofuran derivati," Revista de Chimie 36(8):760-761 (with English Translation).
Majdik et al. (1989). "Prepararea unor 2-(aril)-nitrobenzofurani din 0-(nitrofenil)-acetofenonoxime," Revista de Chemie, vol. 40, No. 8, pp. 689-693 (with English Translation).
Majdik et al. (1989). "0-Arilarea cetoximelor cu nitroclorbenzeni," Revista de Chemie, vol. 40, No. 6, pp. 490-493 (with English Translation).
March (Jul. 1, 1992). "Aromatic Electrophilic Substitution," Chapter 11 in *Advanced Organic Chemistry, Reactions, Mechanism and Structure*, 4th edition, Wiley lnterscience, pp. 538-542.
March (Jul. 1, 1992). "Aliphatic Nucleophilic Substitution," Part 2 in *Advanced Organic Chemistry, Reactions, Mechanism and Structure*, 4th edition, Wiley lnterscience, pp. 442.
Marvel et al. (1941). "Diphenylacetic Acid," Org. Synth. Coll. vol. 1, 224-225.
Mehrotra et al. (2001). "Search for new chemical entities as menses inducing agents," Contraception. 64:187-191.
Munch et al. (1946). "The Preparation of Some α-Dialkylamino-ω-Methylaminoalkanes," J. Am. Chem. Soc. 68:1297-1299.
Nagy et al. (2007). "Isomorphous Substitution in Zeolites," *Mol. Sieves* 5:365-478.
Nakamura et al. (2004). "Pyrazole Derivatives as new potent and selective 20-hydroxy-5,6,11,14-Eicosatetraenoic Acid Synthase Inhibitors," *Bioorganic Medic. Chem.* 12:6209-6219.
Pal et al. (2007). "Synthesis of monohydroxy-functionalized triphenylene discotics: green chemistry approach," Tetrahedron 63:6874-6878.
Roshchin et al. (1998). "Synthesis of Benzofurans via Pd2+-Catalyzed Oxidative Cyclization of 2-Allylphenols," Journal of Organometallic Chemistry 560(1-2):163-167.
Sanfilippo (1988). "Synthesis of (aryloxy)alkylamines. 1. Novel antisecretory agents with H+K+-ATPase inhibitory activity," J. Med. Chem. 31(9):1778-1785.
Serajuddin (2007). "Salt formation to improve drug solubility," Advanced Drug Delivery Reviews 59:603-616.
Shridhar (1981). "Synthesis & Biological Activity of Some New 2-[(5-Nitro-2-furyl- & 5-nitro-2-thienyl)vinyl]-N-arylsulphonamides & 1-[2-(5-Nitro-2-furyl & 5-nitro-2-thienyl)vinyl]sulphonyl Heterocycles," Indian Journal of Chemistry 208:234-237.

Skeels et al. (1989). "Zeolite Chemistry, Substitution of iron or titanium for Aluminum in Zeolites via reaction with the respective ammonium fluoride salts," *ACS Symposium series, zeolite Synthesis* 398:420-435.
Ślusarska et al. (Feb. 1981). "One-Pot Phase-Transfer-Catalysed N-Alkylation of Diphenylphosphinamide with Alcohols in the Presence of Methanesulfonyl Chloride," *Synthesis* 155-156.
Son et al. (1989). "Stereochemical Mechanism of lodoacetic Acid Mediated Decomposition of $_L$-Methionine to $_L$-Homoserine Lactone," *Journal of the American Chemical Society* 111(4):1363-1367.
Sun et al. (2004). "N-{2-[2-( 4-Phenylbutyl)benzofuran-4-yl]cyclopropylmethyl}-acetamide: an orally bioavailable melatonin receptor agonist," Bioorganic & Medicinal Chemistry Letters 14:5157-5160.
Tanaka (1967). Studies on 5-Aminosalicylaldehyde Derivatives. II. Reduction of 5-(p-Sulfophenylazo)salicylaldehyde Through Poly(5-Nitrilosalicylidene) to 5-Aminosalicylaldehyde Derivatives, Bulletin of the Chemical Society of Japan 40(7):1724-1726.
Thornber (1979). "Isosterism and molecular modification in drug design." Chem. Soc. Rev. 8:563-580.
Upthagrove et al. (Nov. 2001). "Importance of Amine $pK_a$ and Distribution Coefficient in the Metabolism of Fluorinated Propranolol Derivatives. Preparation, Identification of Metabolite Regioisomers, and Metabolism by CYP2D6," Drug Metab. Dispos. 29(11):1377-1388.
Wamser et al. (1989). "Kinetics and Mechanisms for the Two-phase Reaction between Aqueous Aniline and Benzoyl Chloride in Chloroform, with and without Pyridine Catalysis," J. Org. Chem. 54:150-154.
Weissman et al. (2005). "Recent advances in ether dealkylation," Tetrahedron 61:7833-7863.
Weitkamp et al. (1986). "Isomorphe Substitution in Zeolithen: Katalyse an Boro-, Alumo-und Galio-Silicaten mit ZSM-5-Strukter," Chem. Ing. Tech. 58(12):969-971 (with English Translation).
Wikipedia. (Nov. 5, 2012). "Reduction of Nitro Compounds.".
Wu et al. (2004). "Immobilization of HX: [Hmim]X as Halogenating Agent, Recyclable Catalyst and Medium for Conversion of Alcohols to alkyl halides," Chinese J. Chem. 22:619-621.
Wuts (2006). Greene's Protective Groups in Organic Synthesis, Fourth Edition, John Wiley and Sons, Chapter 7, Protection for the Amino Group, pp. 696-926.
Yang et al. (2009). "Structure-based virtual screening for identification of novel 11 β-HSD1 inhibitors," European J. of Medicinal Chem. 44(3):1167-1171.
Yin et al. (2000). "Palladium-Catalyzed Intermolecular Coupling of Aryl Halides and Amides," Organic Letters 2(8):1101-1104.
Yin et al. (2002). "Pd-Catalyzed Intermolecular Amidation of Aryl Halides: The Discovery that Xantphos Can Be Trans-Chelating in a Palladium Complex," Journal of the American Chemical Society 124:6043-6048.
Zasshi (1956). "Studies on the Syntheses of Phenothiazine Derivatives. I. Syntheses of N-Substituted Phenothiazines by Tosylates," *J. Pharm. Soc. of Japan* 76:637-640 (with English Translation).
U.S. Appl. No. 14/377,484, filed Aug. 7, 2014, by Huszar et al.
U.S. Appl. No. 14/945,222, filed Nov. 18, 2015, by Friesz et al.
U.S. Appl. No. 14/946,510, filed Nov. 19, 2015, by Friesz et al.
Landge et al. (2013) "Stability Indicating RP-HPLC Method for the Determination of Dronedarone Hydrochloride and its Potential Process-Related Impurities in Bulk Drug and Pharmaceutical Dosage Form," *American Journal of Analytical Chemistry* 4:323-335.
Li et al. (2011) "Synthesis of Dronedarone Hydrochloride," *Chinese Journal of Pharmaceuticals* 42(3):161-164 (English abstract).

* cited by examiner

PROCESS FOR PREPARATION OF DRONEDARONE BY N-BUTYLATION

CROSS REFERENCE TO RELATED APPLICATIONS

This application is a divisional patent application of U.S. patent application Ser. No. 14/007,814 (U.S. Pat. No. 9,174,959), filed Dec. 6, 2013, which also adopts the international filing date of Mar. 27, 2012, which is a National Phase application under 35 U.S.C. §371 of International Application No. PCT/HU2012/000020 filed Mar. 27, 2012, which claims priority benefit to Hungary Application No. P11 00165 filed Mar. 29, 2011, the disclosures of each of which are herein incorporated by reference in their entirety.

FIELD OF THE INVENTION

This invention relates to a novel process for the preparation of dronedarone and pharmaceutically acceptable salts thereof, to novel intermediary compounds used in this process and their preparation.

TECHNICAL BACKGROUND

Dronedarone is a known drug for the treatment of arrhythmia and has the chemical name of N-[2-n-butyl-3-[4-[3-(di-n-butylamino)propoxy]benzoyl]benzofuran-5-yl]methane-sulfon-amide [see also formula (I) below]. There are some known processes for the preparation of dronedarone as follows:

In EP 0471609 the following scheme is disclosed for the preparation of dronedarone [Process A]

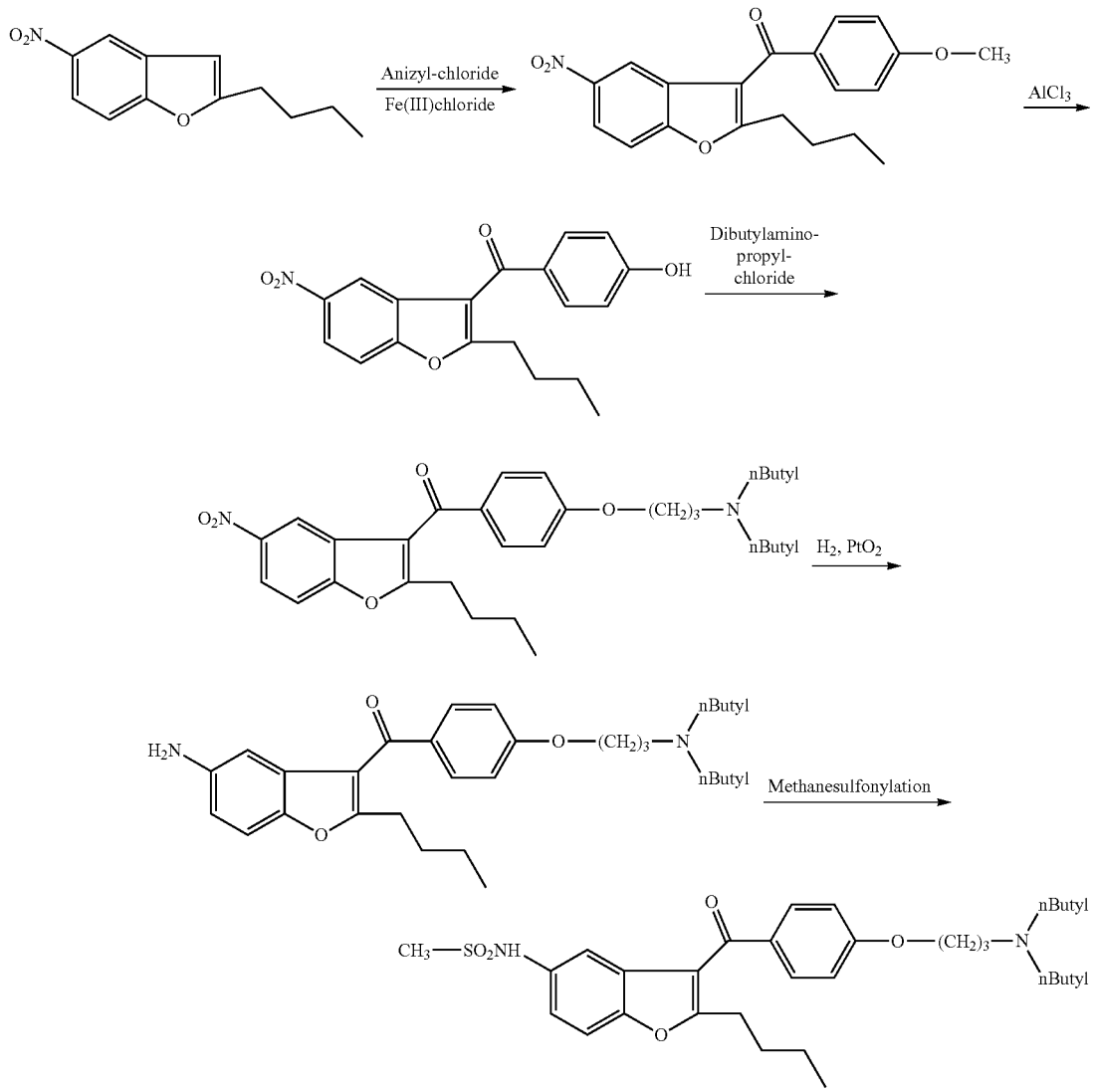

The above mentioned patent description discloses some new intermediary compounds, too.

In WO 02/48078 the following scheme is disclosed for the preparation of dronedarone [Process B]:

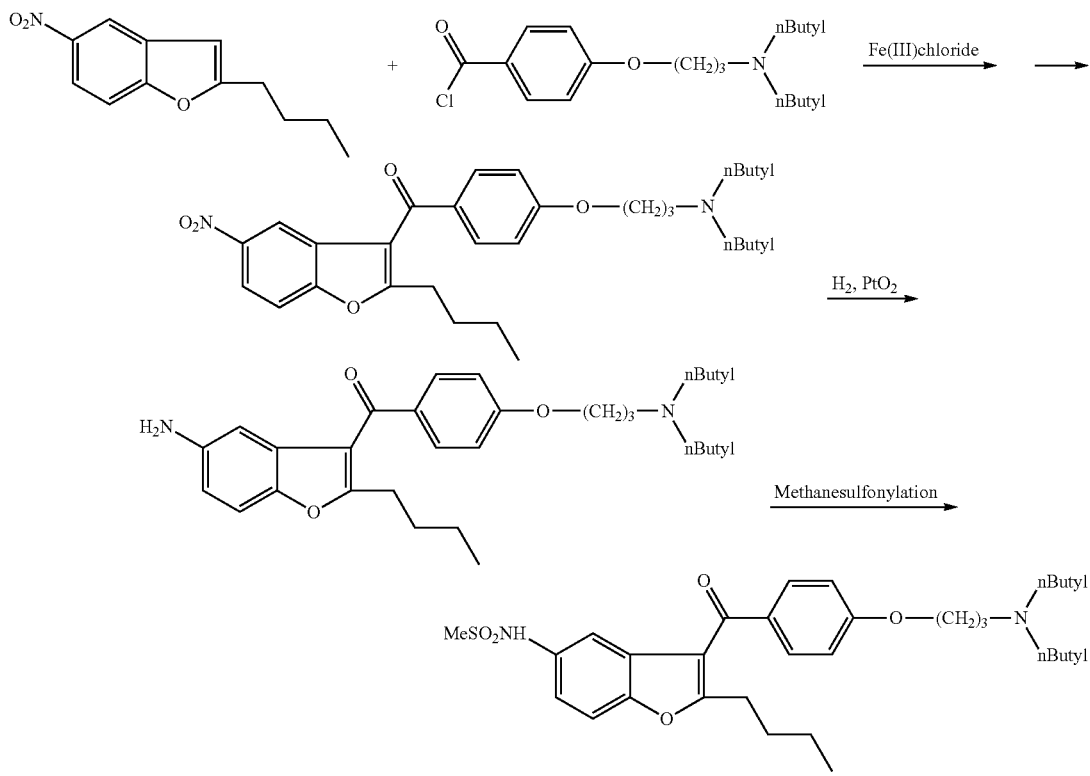

The novelty of the process is based on the adaptation of the Friedel-Crafts reaction in the first step. The process and the intermediary compounds used for the preparation of the benzoylchloride compound of the first step are disclosed, too, in this document. The further steps of the process are identical with the final steps of the synthetic route disclosed in EP 0471609 [Process A], but in the claims the whole synthetic route is claimed, up to dronedarone.

In WO 02/48132 (Sanofi) the following reaction route is disclosed [Process C]. This method is the so called super-convergent route. In the first step of it 5-amino-2-butyl-benzofuran

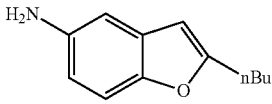

is mesylated and the obtained 2-butyl-5-methanesulfona-mido-benzofuran (in HCl salt form) is further reacted in the next step as follows:

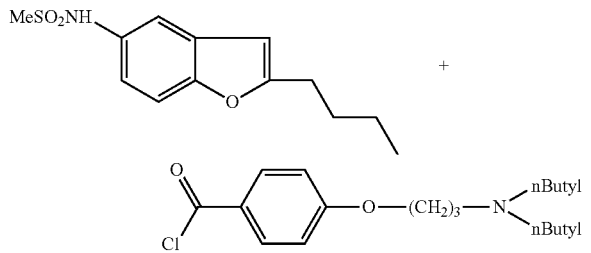

In this process the order of reaction steps are altered, the reduction and the methansulfonylation steps are performed at the beginning of the procedure. Besides the reaction route for preparation of dronedarone, the starting material 2-butyl-5-methansulfonamido-benzofuran and its preparation is also claimed.

From among the mentioned procedures the first one [Process A] is the so called linear synthesis. In this way of procedure the different parts of the dronedarone are stepwise built up on the starting compound. This method is the least economical because the step by step building of the chemical groups is performed where more and more complicated and expensive molecules are applied which rises the costs of preparation. Furthermore, it comprises complicated and dangerous reaction step because aluminium chloride is used in the cleaving reaction of the methoxy group which makes the industrial feasibility more complicated.

In WO 02/48078 (Process B) a shorter synthetic route is disclosed which makes this process more economical, but its last reaction step remained the methansulfonylation reaction of the amino group. This reaction step (see the method described in example 6 of WO 02/48078) is complicated and give a low yield, only 61.6%. Pure product can be obtained after purification using chromatographic column purification, which method is necessary because of the separation difficulties of the bis-methanesulfonylated product.

The process disclosed in WO 02/48132 (process C) is simpler and more economical taken into consideration the number of the reaction steps. Unfortunately, in the last reaction step rather impure dronedarone.HCl (hydrochloride salt) is formed which is the obvious consequence of the presence of dibutylamino group in the Friedel-Crafts reaction. According to Examples 3 and 4, the crude dronedarone hydrochloride salt is prepared with a yield of 90% which was further purified and finally the crude dronedarone base was produced with a yield of 86%. This base is reacted with hydrogen chloride gas dissolved in isopropanol which results in pure dronedarone hydrochloride salt. No yield was given for this reaction step. According to example 5 crude dronedarone hydrochloride salt was prepared with a yield of 90%, which was washed with water and reacted with hydrogen chloride gas dissolved in isopropanol, resulting dronedarone hydrochloride salt again. The quality of this product is not known. However, neither the components used in the Friedel-Crafts reaction nor the resulted products and by-products are soluble in water, the washing step with water cannot result any purification apart from the removal of inorganic salts.

There is another drawback of this process, namely, a dimesylated side-product is formed in the mesylation reaction of the 5-amino-2-butyl-benzofuran. The purification is carried out by crystallization which has a yield of 78.5%.

It is an object of the present invention to provide a novel process for the preparation of dronedarone of formula (I), starting with known and commercially available materials, applying simple and environmentally compatible reagents and solvents to afford high overall yields and good purity of the product.

SUMMARY OF THE INVENTION

The main aspect of the invention is a process for the preparation of dronedarone (I) and pharmaceutically acceptable salts thereof

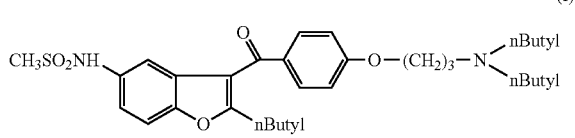
(I)

which comprises reacting the compound of formula (II) or salt thereof

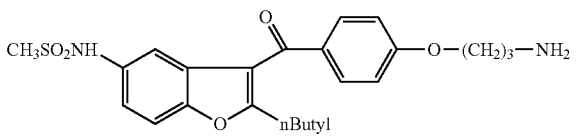
(II)

with a compound of formula L-(CH$_2$)$_3$—CH$_3$ (III), where L is a leaving group, isolating the obtained product as a base and, if desired, converting it into a pharmaceutically acceptable salt thereof.

The present invention avoids the drawbacks of the procedures mentioned before, because the formation of dronedarone in the final step is completed with a butanol derivative, e.g. organic and inorganic esters of butanol. We have found surprisingly that compounds of formula (III) can be connected to the amino group of the compound of formula (II) in a way where connection takes part only on the free amino group [see the "right" side of formula (II)] and not on the sulphonamide group [see the "left" side of formula (II)].

Compounds of formula (III) can be purchased or can be prepared by known methods (J. of Steroid Biochemistry and Molecular Biology 80, (2002), 429-440; Synthesis (1979, 882). Starting materials of formula (III) are also known from EP 0471609 and compound of formula (X) from WO 02/48132.

Further aspects of the invention are the novel intermediary compounds and the methods for the preparation thereof (see below in the "Detailed description of the invention" part).

DETAILED DESCRIPTION OF THE INVENTION

Therefore the present invention relates to a process for the preparation of dronedarone and pharmaceutically acceptable salts thereof. The whole process—starting from compounds available commercial sources—reads as follows:

A) For the preparation of compounds of formula (V)

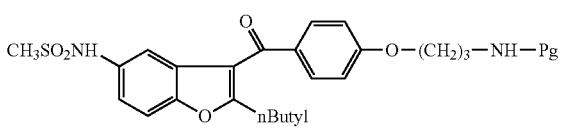
(V)

the compound of formula (X)

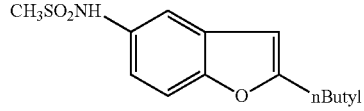
(X)

is reacted with compound of formula (XI)

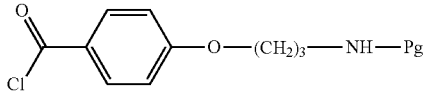
(XI)

under Friedel-Crafts reaction conditions, where Pg is amino protecting group, typically an A-CO— group, where A is alkyl, alkoxy, aryl or aryloxy group, e.g. it is ethoxycarbonyl.

The reaction is carried out halogene and/or nitro group containing solvents, e.g. dichloromethane, dichloroethane, chlorobenzene, nitromethane, nitrobenzene. Catalyst also can be applied, e.g. AlCl$_3$, FeCl$_3$, SnCl$_4$, TiCl$_4$.

Compound (II) can be prepared from the above compound (V) by removing Pg (see below).

Another way for the preparation of compound (II) reads as follows:

B) For the preparation of compound of formula (VII)

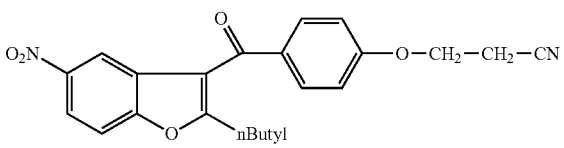
(VII)

a compound of formula (VIII)

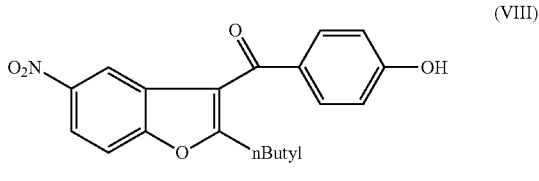

is reacted with acrylonitrile of formula of $CH_2=CH-CN$ (IX).

Compound (VIII) is known from EP 0 471 609 (Sanofi).

Typically the reaction is carried out in a solvent (which can be e.g. a $C_{1-4}$ alcohol, typically methanol or ethanol), and typically a strong basic catalyst is applied. This catalyst is selected typically from the group of alkali alkoxydes and quaternary ammonium hydroxides, and it can be e.g. benzyltrimethylammonium hydroxide.

Typically the reaction is carried out in the excess of acrylonitrile as solvent at the boiling point of the solvent, e.g. about 70 to 90° C. Typically strong water free ammonium quaternary hydroxides or alkali alkoxydes can be applied as catalyst.

C) For the preparation of compound of formula (VI)

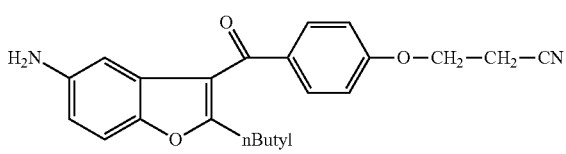

an above compound of formula (VII) is hydrogenated.

The reaction is carried out among usual hydrogenation conditions. For example, the hydrogenation process is carried out in a solvent in the presence of catalyst, e.g. Pd or Pt catalyst, typically Pd/C. Typically the solvent is selected from the group of $C_{1-4}$ alcohols, ethyl acetate and cyclohexane, e.g. the solvent is methanol or ethanol.

D) For the preparation of compound of formula (IV)

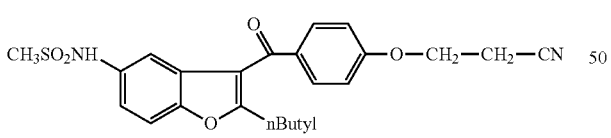

an above compound of formula (VI) is mesylated.

Typically the reaction is carried out in an indifferent solvent, typically in the presence of an acid binding agent. In a practical embodiment the solvent is selected from the group of dichloromethane, dichloroethane and chlorobenzene. Typically the acid binding agent is a tertiary nitrogen base, for example pyridine or triethylamine.

In the process a mesylating reagent should be applied. It can be any reagent which can be used for inserting a $CH_3SO_2-$ group into the free amino group of compound of formula (VI). It is practical to use methanesulfonic anhydride or methanesulfonyl halogenide, e.g. methanesulfonyl chloride.

E) For the preparation of compound of formula (II)

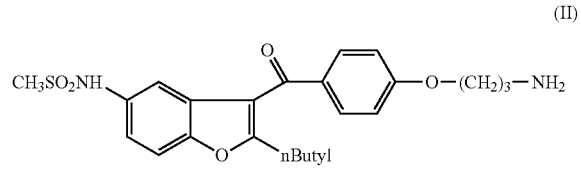

the above compound of formula (IV) is hydrogenated.

The reaction is carried out among usual hydrogenation conditions. For example the hydrogenation process is carried out in a solvent in the presence of catalyst, e.g. Ni catalyst, which is typically Raney-Ni. Typically the solvent is selected from the group of $C_{1-4}$ alcohols, ethyl acetate and cyclohexane; e.g. the solvent is methanol or ethanol.

E') Alternatively, compound of formula (II) can be prepared from another starting material, namely a compound of formula (V)

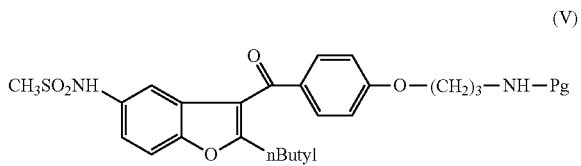

where Pg amino protecting group, is deprotected by any known method.

The Pg amino protecting group is typically an A-CO— group, where A is alkyl, alkoxy, aryl or aryloxy group, e.g. it is ethoxycarbonyl.

The Pd protective group can be removed according to known methods, e.g. by acidic or alkaline hydrolysis (see e.g. the following book: Philip J. Kocienski, Protecting Groups, 2005).

F) Finally, for the preparation of dronedarone of formula (I) and pharmaceutically acceptable salts thereof

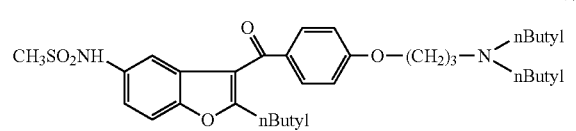

an above compound of formula (II) or a salt thereof is reacted with a compound of formula L-$(CH_2)_3$—$CH_3$ (III), where L is a leaving group, then the obtained product is isolated as a base and, if desired, converted it into a pharmaceutically acceptable salt thereof.

Typical meanings of L are selected from the group of halogen, methanesulfonyloxy, trifluoromethanesulfonyloxy and benzenesulfonyloxy, optionally substituted with halogen, alkyl, alkoxy, nitro or protected amino group.

In another embodiment the reaction step F is carried out in a solvent (or solvent mixture), optionally in the presence of a base and/or catalyst. In another embodiment the reaction is carried out in a solvent and both base and catalyst is applied.

The above solvent typically is selected from the group of ketones, alcohols, esters, amides, ethers, dimethylsulfoxide and aromatic solvents and any mixtures thereof. In a specific embodiment the solvent is a ketone, e.g. acetone or methylethylketone. In another embodiment the solvent is an alcohol, e.g. methanol, ethanol, isopropanol or n-butanol.

Typically the reaction is carried out in the presence of a base, which can be selected from the group of nitrogen-containing bases, e.g. from the group of pyridine, 2-methyl pyridine and triethylamine.

In another embodiment L is halogen, e.g. chlorine, and the reaction is carried out in the presence of a catalyst, which can be selected from the group of alkyl iodides, e.g. it is sodium iodide.

The temperature applied in the reaction is typically between 0° C. and the boiling point of the solvent (which can be a solvent mixture, as it was mentioned above), e.g. between 60-120° C. Typically the atmospheric pressure is applied during the reaction.

The applicable acid for the preparation of pharmaceutically acceptable salts can be any inorganic or organic acid which forms an acid addition salt with the compound of general formula (I). Exemplary acids which can form an acid addition salt are as follows: acetic acid, adipic acid, alginic acid, ascorbic acid, aspartic acid, benzoic acid, benzenesulfonic acid, methansulfonic acid, ethansulfonic acid, boric acid, butyric acid, citric acid, fumaric acid, hydrogen chloride, hydrogen bromide, hydrogen iodide, 2-hydroxyethanesulfonic acid, maleic acid, oxalic acid, nitric acid, salicylic acid, tartaric acid, sulfuric acid (forming sulfate or bisulfate anion), sulfonic acid (such as those mentioned herein), succinic acid, toluenesulfonic acid and the like. The hydrogen halogenide salts are typical, especially the hydrogen chloride salt.

Here it is mentioned that on the mesylate group of compound of general formula (I) (see the "left side" of the molecules) a salt formation can be carried out (on the amide part of it) by a strong base, e.g. an alkaline hydroxide, typically by sodium hydroxide. However, these salts have less practical importance, but they are within the scope of salts. It means that the phrase "salts" embraces both the acid addition salts and the salts formed by bases (basic salts) in case of compounds of general formula (I).

As it was mentioned above the further starting materials are commercially available or can, be prepared by applying known synthetic ways, e.g. as it is given in the relating examples 10 to 13.

Other objects of the invention are the novel intermediary compounds applied in the processes, namely the following compounds:

Compound of formula (II) and salts thereof

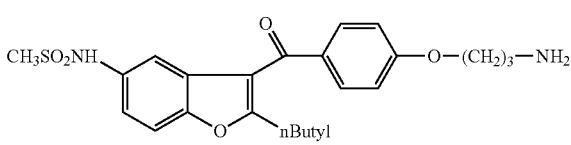

(II)

Compound of formula (IV) and salts thereof

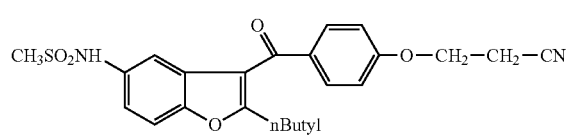

Compounds of formula (V) and salts thereof

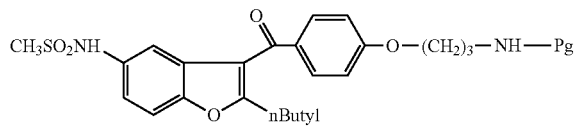

(V)

where Pg is an amino protecting group, typically an A-CO— group, where A is alkyl, alkoxy, aryl or aryloxy group, e.g. it is ethoxycarbonyl.

Compound of formula (VI) and salts thereof

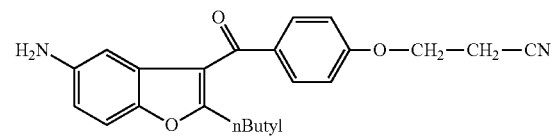

(VI)

Compound of formula (VII)

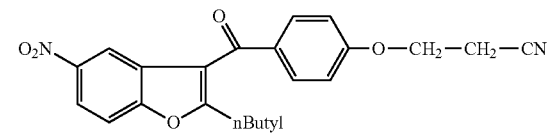

(VII)

Other objects of the invention are the processes for the preparation of the novel intermediary compounds, namely the following ones:

Process for preparation of compound of formula (II) and salts thereof where
a) the compound of formula (IV)

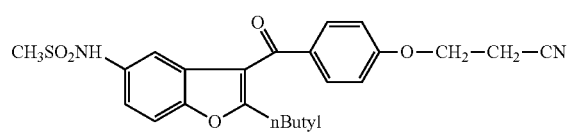

(IV)

is hydrogenated or
b) a compound of formula (V),

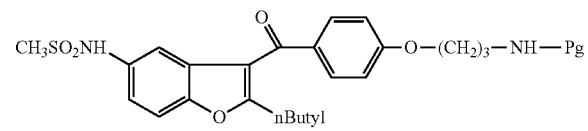

(V)

is deprotected, where Pg is an amino protecting group.

The hydrogenation and the deprotection can be carried out as it was disclosed above in point E) and in point E'), respectively.

Process for preparation of compound of formula (IV) and salts thereof where the compound of formula (VI)

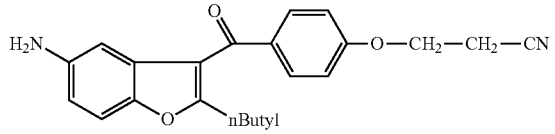
(VI)

is mesylated.

The mesylation can be carried out is as it was disclosed above in point D).

Process for preparation of compounds of formula (V) and salts thereof where the compound of formula (X)

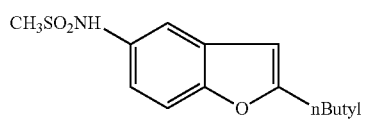
(X)

is reacted with a compound of formula (XI)

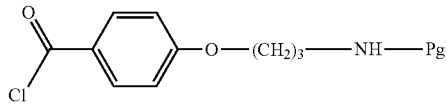
(XI)

under Friedel-Crafts reaction conditions, where Pg is amino protecting group, typically an A-CO— group, where A is alkyl, alkoxy, aryl or aryloxy group, e.g. it is ethoxycarbonyl.

The reaction can be carried out is as it was disclosed above in point A).

Process for preparation of compound of formula (VI) and salts thereof, where the compound of formula (VII)

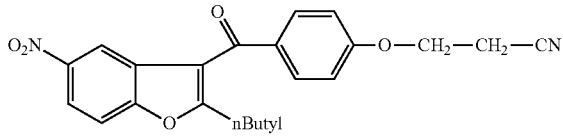
(VII)

is hydrogenated.

The hydrogenation can be carried out is it was disclosed above in point C).

Process for preparation of compound of formula (VII), where the compound of formula (VIII)

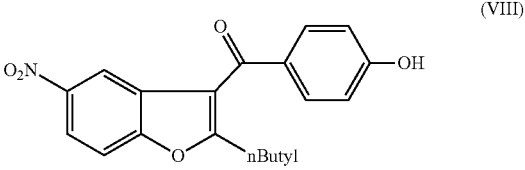
(VIII)

is reacted with acrylonitrile of formula CH$_2$=CH—CN (IX).

The reaction can be carried out is it was disclosed above in point B).

In the processes for the preparation of the intermediary compounds the product is isolated as a base typically (if the compound has a free amino or an alkylated amino group). If desired, the isolated base can be converted into a salt (acid addition salt) thereof, which is typically a pharmaceutically acceptable salt [the possible acids are mentioned in point F)]. Theoretically the acid addition salt can be prepared directly if the relating acid is in the final reaction mixture from which the solid product is made (however, this way is not applied in case of these compounds where the base type form has practical importance).

Here it is mentioned that some of the above intermediary compounds have a mesylate group (see the "left side" of the molecules) where a salt formation can be carried out (on the amide part of it) by a strong base, e.g. an alkaline hydroxide, typically by sodium hydroxide. However, these salts have less practical importance, but they are within the scope of salts which can be prepared by the claimed process, i.e. the phrase "salts" embraces the salts formed by bases (basic salts) in such cases (where the molecule has a mesylate group).

In the above reactions the temperature is chosen according to the general practice of a person skilled in organic chemistry. Typically the temperature is between 10° C. and the boiling point of the applied solvent (which can be the mixture of the mentioned solvents in a specific embodiment). Applicable temperature values can be found in the examples.

All the above reactions are carried out under atmospheric pressure with the exception of the hydrogenation steps where higher pressure also can be applied, typically up to 20 bar, e.g. 5 to 10 bar.

As used herein, the term alkyl includes straight or branched aliphatic hydrocarbon chains of 1 to 6 carbon atoms, e.g., methyl, ethyl, isopropyl and t-butyl.

As used herein, the term "alkoxy" includes alkyl-O— groups. Non-limiting examples of suitable alkoxy groups include methoxy, ethoxy, n-propoxy, isopropoxy and n-butoxy.

As used herein, the term "aryl" includes aromatic monocyclic or multicyclic ring systems comprising 6 to about 14 carbon atoms, preferably 6 to about 10 carbon atoms. Non-limiting examples of suitable aryl groups include phenyl and naphthyl.

As used herein, the term "aryloxy" includes aryl-O— groups.

As used herein, the term "halogen" includes fluoro, chloro, bromo and iodo atoms.

EXAMPLES

Example 1

N-[2-butyl-3-{4-[(3-dibutylamino)propoxy]benzoyl}-1-benzofuran-5-yl]methanesulfonamide (I)

1 g of N-[2-butyl-3-{4-[(3-amino)propoxy]benzoyl}-1-benzofuran-5-yl]-methansulfonamide (II) is dissolved in 5 ml of methyl ethyl ketone. 0.18 g of pyridine and 0.34 g of sodium iodide are added and the mixture is heated to boiling point. 0.62 g of 1-bromobutane (III) dissolved in 1 ml of methyl ethyl ketone is added at this temperature during 15 minutes and the mixture is boiled for 16 hours. The reaction mixture is evaporated, 20 ml of water and 20 ml of dichloromethane are added. The organic phase is washed with 5 ml of 5% $NaHCO_3$ solution, separated and evaporated. The product is purified by forming its oxalate salt as follows: to the residue 4 ml of methylethyl ketone is added and the mixture heated to 70. To this solution 0.24 g of oxalic acid dissolved in 1.5 ml of methylethyl ketone is added at 70° C. After cooling to 20° C. in 6 hours the mixture is stirred at 10° C. for 1 hour and filtered. To the obtained oxalate salt 2.5 ml of water and 4 ml of dichloromethane and 0.63 g of potassium carbonate are added. After stirring for 30 minutes the separated potassium oxalate is filtered and washed with 2 ml of dichloromethane and the solvent is evaporated.

Yield: 1.1 g (88%). Purity of the oxalate salt: 99.8% (HPLC).

1H NMR (DMSO): 0.8-0.9 ppm (m, 9H); 1.2-1.5 ppm (m, 10H); 1.67 ppm (5', 2H); 1.87 ppm (5', 2H); 2.38 ppm (t, J=7.2 Hz, 4H); 2.57 ppm (m, 2H); 2.88 ppm (t, J=7.5 Hz, 2H); 2.91 ppm (s, 3H); 9.51 ppm (t, J=6.2 Hz, 2H); 7.09 ppm (d, J=8.8 Hz, 2H); 7.24 ppm (dd, J=8.9, 2.2 Hz, 1H); 7.38 ppm (d, J=2.1 Hz, 1H); 7.65 ppm (d, J=8.8 Hz, 1H); 7.81 ppm (d, J=8.8 Hz, 2H)

Example 2

N-[2-butyl-3-{4-[(3-dibutylamino)propoxy]benzoyl}-1-benzofuran-5-yl]methanesulfonamide (I)

0.8 g of N-[2-butyl-3-{4-[(3-amino)propoxy]benzoyl}-1-benzofuran-5-yl]methanesulfonamide (H) is dissolved in 5 ml of n-butanol. 0.15 g of pyridine is added and the mixture is heated to 70° C. at this temperature 0.68 g of butyl-methanesulfonate (III) dissolved in 1 ml of n-butanol is added during 15 minutes and the mixture is kept at 70° C. for 14 hours. [The methanesulfonate is prepared according to the procedure described in J. of Steroid Biochemistry and Molecular Biology 80 (2002) 429-440.] The reaction mixture is evaporated and 20 ml of dichloromethane and 10 ml of water is added. The phases are separated. The organic phase is washed with 10 ml of $NaHCO_3$ of 5%. The organic phase is evaporated. The product is purified by on silica gel (ethyl acetate/hexane; 1:3 v/v).

Yield: 0.79 g (79%). Purity: 100% (HPLC).

The product is identical with the compound prepared in example 1.

Example 3

N-[2-butyl-3-{4-[(3-dibutylamino)propoxy]benzoyl}-1-benzofuran-5-yl]methanesulfonamide (I)

The process is performed according to example 2 with the difference that instead of 0.68 g of butyl methanesulfonate 1.0 g of butyl-(4-toluene-sulfonate) (III) is added [prepared according to the method in Synthesis (1979), 11, 882]. Yield of purified product: 0.81 g (81%). Purity: 100% (HPLC).

Example 4

N-[2-butyl-3-{4-[(3-dibutylamino)propoxy]benzoyl}-1-benzofuran-5-yl]methanesulfonamide (I)

The process is performed according to example 1 with the difference that instead of 0.15 g of pyridine 0.22 g of triethylamine is used.

Yield of purified product: 1.04 g (83%). Purity: 100% (HPLC).

Example 5

N-[2-butyl-3-{4-[(3-amino)propoxy]benzoyl}-1-benzofuran-5-yl]methanesulfon-amide 3.0 g of N-[2-butyl-3-{4-[2-cyanoethoxy]benzoyl}-1-benzofuran-5-yl]methanesulfonamide (IV) is dissolved in 300 ml of methanol and 5 g of Raney-Ni catalyst is added. The mixture is stirred at 25° C. at 10 bar $H_2$ pressure for 24 hours. The catalyst is filtered, and the solvent is evaporated.

Yield: 2.94 g (98% %). Purity: 75% (HPLC).

1H NMR (DMSO): 7.77 ppm (d, J=8.7 Hz, 2H); 7.59 ppm (d, J=8.70 Hz, 1H); 7.23 ppm (d, J=2.06 Hz, 1H); 7.18 ppm (dd, J=8.81, 2.17 Hz, 1H); 7.07 ppm (d, J=8.7 Hz, 2H); 4.14 ppm (t, J=6.41 Hz, 2H); 2.85 ppm (s, 3H); 2.80 ppm (t, J=7.10 Hz, 2H); 2.71 ppm (t, J=6.75 Hz, 2H); 1.82 ppm (quin, J=6.52 Hz, 2H); 1.65 ppm (quin, J=7.30 Hz, 2H); 1.24 ppm (5×t, J=7.32 Hz, 2H); 0.80 ppm (t, J=7.32 Hz, 3H)

$[M+H]^+_{found}$=445.1781 Da. $[M+H]^+_{calculated}$=445.1797 Da.

Example 6

N-[2-butyl-3-{4-[2-cyanoethoxy]benzoyl}-1-benzofuran-5-yl]methanesulfonamide (IV)

4.0 g of (5-amino-2-butyl-benzofur-3-yl)-[4-(2-cyanoethoxy)phenyl]methanon (VI) is dissolved in 40 ml of dichloromethane. The mixture is warmed to 30-35° C. and 1.05 g of pyridine is added at this temperature in 5 minutes. At this temperature 1.5 g of methanesulfonyl chloride is added in 5 minutes and the mixture is stirred at 30-35° C. for 3 hours. The mixture is cooled to 20° C. and washed with 2×15 ml of water, 2×15 ml of $NaHCO_3$ of 5% and 1×15 ml of water. The phases are separated and the dichloromethane is evaporated.

Yield: 4.81 g (100%). Purity: 94.8% (HPLC). Mp.: 120.9-121.7° C.

1H NMR (DMSO): 9.6 ppm (s, 1H) 7.79 ppm (d, J=8.93 Hz, 2 H) 7.62 ppm (d, J=8.93 Hz, 1H) 7.27 ppm (d, J=2.06 Hz, 1 H) 7.21 ppm (dd, J=8.70, 2.06 Hz, 1 H) 7.13 ppm (d, J=8.93 Hz, 2 H) 4.31 ppm (t, J=5.84 Hz, 2 H) 3.07 ppm (t, J=5.84 Hz, 2H) 2.88 ppm (s, 3 H) 2.80 ppm (t, J=7.44 Hz, 2 H) 1.65 ppm (quin, J=7.44 Hz, 2 H) 1.24 ppm (s×t, J=7.37 Hz, 2 H) 0.80 ppm (t, J=7.44 Hz 3 H)

Example 7

(5-amino-2-butyl-benzofur-3-yl)-[4-(2-cyanoethoxy)phenyl]methanon (VI)

1 g of (5-nitro-2-butyl-benzofur-3-yl)-[4-(2-cyanoethoxy)phenyl]methanon (VII) is dissolved in 15 ml of methanol and 0.1 g of 10 w/w % wet Pd/C catalyst is added and the reaction mixture is heated to 50° C. with a stirring of 800 round/min. Hydrogen pressure of 5 bar is set in the reactor and the mixture is stirred at this temperature for 2 hours. After cooling to room temperature the catalyst is, filtered off and the solvent is evaporated.

Yield: 0.92 g (100%). Purity (HPLC): 97.3%.

1H NMR (DMSO): 7.76 ppm (d, J=8.93 Hz, 2H); 7.26 ppm (d, J=8.70 Hz, 1H); 7.12 ppm (d, J=8.70 Hz, 2H); 6.57 ppm (dd, J=8.70, 2.29 Hz, 1H); 6.49 ppm (d, J=2.29 Hz, 1H); 4.30 ppm (t, J=5.84 Hz, 2H); 3.06 ppm (t, J=5.84 Hz, 2H); 2.73 ppm (t, J=7.55 Hz, 2H); 1.62 ppm (quin, J=7.50 Hz, 2H); 1.23 ppm (sxt, J=7.28 Hz, 3H); 0.80 ppm (t, J=7.32 Hz, 4H)

$[M+H]^+_{found}$=363.1711 Da. $[M+H]^+_{calculated}$=363.1709 Da.

Example 8

(5-nitro-2-butyl-benzofur-3-yl)-[4-(2-cyanoethoxy)phenyl]methanon (VII)

27.8 g of (2-butyl-5-nitro-1-benzofur-3-yl)-(4-hydroxyphenyl)methanon (VIII), 43.5 g of acrylonitrile and 3.8 g of Triton B (benzyltrimethylammonium hydroxide) are added and heated under stirring to 80-85° C. and stirred at this temperature for 48 hours. After cooling the reaction mixture to room temperature it is evaporated and the acrylonitrile is recovered for the next trial. To the residue 15.0 ml of dichloromethane is added and washed with 3×80 ml of sodium hydroxide of 5%. From the sodium hydroxide solution 16.2 g of starting (2-butyl-5-nitro-1-benzofur-3-yl)-(4-hydroxyphenyl)methanon is recovered.

The dichloromethane solution is evaporated.

Yield: 12.07 g (94.2% for the consumed starting material). Purity: 97.6% (HPLC).

Mp.: 108.6-108.9° C.

1H NMR (DMSO): 0.80 ppm (t, J=7.44 Hz, 3H); 1.24 ppm (sxt, J=7.37 Hz, 2H); 1.68 ppm (quin, J=7.50 Hz, 2H); 2.84 ppm (t, J=7.55 Hz, 2H); 3.07 ppm (t, J=5.95 Hz, 2H); 4.33 ppm (t, J=5.95 Hz, 2H); 7.15 ppm (d, J=8.70 Hz, 2H); 7.84 ppm (d, J=8.70 Hz, 2H); 7.92 ppm (d, 9.84 Hz, 1H); 8.22-8.28 ppm (m, 2H)

Example 9

N-[2-butyl-3-{4-[(3-amino)propoxy]benzoyl}-1-benzofuran-5-yl]methanesulfonamide 4.0 g of N-[2-butyl-3-{4-[(3-ethoxycarbonylamino)propoxy]benzoyl}-1-benzofuran-5-yl]-methanesulfonamide (V) is added to 30 ml of methanol and 0.62 g of sodium hydroxide is dissolved in it. The reaction mixture is boiled for 3 hours and the solvent is evaporated. To the obtained solid material 20 ml of water is added and the pH of the solution is set to pH=6 with 2N HCl solution. The separated oil is extracted with 20 ml of dichloromethane. The dichloromethane is evaporated. The residual material is identical with compound prepared in example 5.

Yield: 2.82 g (82%). Purity: 79% (HPLC).

Example 10

N-[2-butyl-3-{4-[(3-ethoxycarbonylamino)propoxy]benzoyl}1-benzofuran-5-yl]methane-sulfonamide (V)

1.6 g of N-(2-butyl-1-benzofuran-5-yl)methanesulfonamide (X) and 15 ml of dichloromethane is stirred at room temperature for 5 minutes. To this suspension 2.4 g of 4-[(3-carbethoxyamino)-propoxy]benzoylchloride (XI) is added at a slow rate. The mixture is cooled down to 5° C. and 1.21 g of Fe(III)chloride is added in 4 portions in 20 minutes at a temperature of 5-10° C. The mixture is stirred for additional 3 hours at 20° C. The mixture is heated to 40-45° C. and 27 ml of water is added in 20 minutes. The reaction mixture is stirred at this temperature for 30 minutes. The phases are separated and the organic phase is washed with 1×8 ml of water, 2×8 ml of NaHCO₃ of 5% and with 2×8 ml of water. The solvent is evaporated. The residual material is purified with chromatography.

Yield of purified product: 2.23 g (72.1%). Purity (HPLC): 91.2%.

Mp.: 155.7-156.9° C.

1H NMR (DMSO): 9.57 ppm (s, 1H); 7.77 ppm (d, J=8.7 Hz. 2H); 7.61 ppm (d, J=8.8 Hz. 1H); 7.27 ppm (d, J=1.6 Hz, 1H); 7.20 ppm (dd, J=8.8, 2.1 Hz, 1H); 7.17 ppm (t, 5.0 Hz, 1H); 7.06 ppm (d, J=8.6 Hz, 2H); 4.09 ppm (t, J=6.2 Hz, 2H); 3.97 ppm (q, J=7.1 Hz, 211); 3.15 ppm (q, J=6.2 Hz, 2H); 2.88 ppm (s, 3H); 2.80 ppm (t, J=7.4 Hz, 2H); 1.88 ppm (5', H=6.4 Hz, 2H); 1.65 ppm (5', J=7.4 Hz, 2H); 1.23 ppm (6', J=7.4 Hz, 2H); 1.14 ppm (t, J=7.0 Hz, 3H); 0.80 ppm (t, J=7.3 Hz, 31-1)

Example 11

4-[(3-carbethoxyamino)propoxy]benzoic acid (XII)

0.4 g of sodium hydroxide and 1.06 g of sodium carbonate is dissolved in 8 ml of water. 1.15 g of 4-[3-aminopropoxy]benzoic acid (XIII) is added to this solution under stirring. The mixture is cooled to 10° C. and stirred at this temperature for 1 hours. 1.09 g of ethoxycarbonyl chloride is added in 20 minutes and the mixture is stirred at 25° C. for 3 hours. The mixture is extracted with 25 ml of dichloromethane and the phases are separated. The pH of the aqueous solution is set to pH=1 with diluted hydrochloride acid and the precipitated white material is stirred in the suspension formed at 10° C. for 1 hours and filtered, washed with 0.3×10 ml of water and dried under reduced pressure at 70° C.

Yield: 1.28 g (81%). Purity (HPLC): 92.8%. Mp.: 147.9-149.1° C.

1H NMR (DMSO): 12.6 ppm (w, 1H); 7.87 ppm (d, 8.8 Hz, 2H); 7.16 ppm (t, J=5.6 Hz, 1H); 6.99 ppm (d, J=8.8 Hz, 2H); 4.05 ppm (t, J=6.2 Hz, 2H); 3.96 ppm (q, J=7.1 Hz, 2H); 3.13 ppm (q, J=6.1 Hz, 2H); 1.86 ppm (5', J=6.5 Hz, 2H); 1.14 ppm (t, J=7.0 Hz, 3H)

Example 12

4-(3-aminopropoxy)benzoic acid HCl salt (XIII)

24.5 g of methyl[4-3(aminopropoxy)benzoate] (XIV) is added to a aqueous solution prepared from 8.4 g of sodium hydroxide and 33.6 ml of water. 56 ml of methanol is added under stirring and the mixture is boiled for 6 hours. The solvent is evaporated. To the solid residue 150 ml of water is added and the solution is extracted with 20 ml of dichloromethane. The pH of the aqueous solution is set to pH=1 with diluted hydrochloric acid. The separated material is washed with 3×100 ml of water and dried under reduced pressure at 70° C.

Yield: 23.2 g (85.8%). Purity: 87% (HPLC). Mp.: 270.0-279.8° C.

Example 13

Methyl[4-(3-aminopropoxy)benzoate] (XIV)

2.1 g of methyl(2-cyanoethoxy)benzoate (XV) (prepared according to the method disclosed in Japanese Patent Appl. No. 19660803) is dissolved in 30 ml of methanol. 0.5 g of Raney-Ni is added and the mixture is hydrogenated at 50° C. under 10 bar of hydrogen pressure for 4 hours. The catalyst is filtered and the solvent evaporated. The product is obtained as an oil. [Helv. Chim. Acta, Vol. 66., Fasc. 2(1983) No. 42.]

Yield: 2.14 g (100%). Purity: 84% (HPLC).

The invention claimed is:

1. A compound of formula (II) or a salt thereof

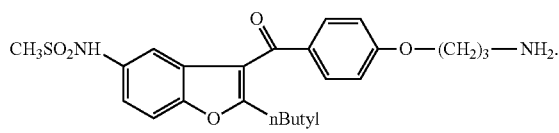
(II)

2. A process for the preparation of a compound of formula (II) or a pharmaceutically acceptable salt thereof

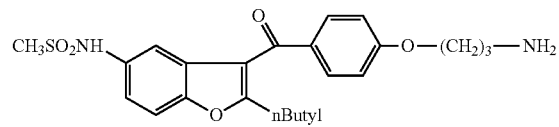
(II)

comprising the steps of:

a) hydrogenating the compound of formula (IV)

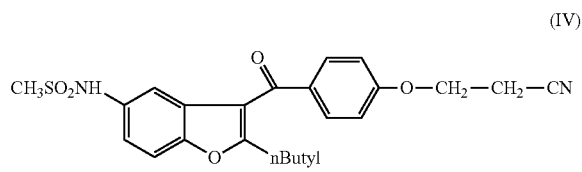
(IV)

or deprotecting a compound of formula (V)

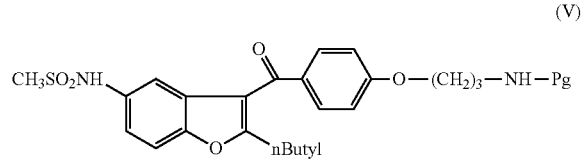
(V)

where Pg is an amino protecting group, b) isolating the obtained product, and c) optionally converting the product into a pharmaceutically acceptable salt thereof.

* * * * *